United States Patent [19]

Skukalek

[11] 4,422,766
[45] Dec. 27, 1983

[54] METHOD OF AND DEVICE FOR REDUCING APPARATUS RESPONSE TIME DURING THE TESTING FOR MOISTURE CONTENT IN MOVING SPACED PLASTIC SHEETS

[75] Inventor: Edward M. Skukalek, Ford City, Pa.
[73] Assignee: PPG Industries, Inc., Pittsburgh, Pa.
[21] Appl. No.: 286,448
[22] Filed: Jul. 27, 1981
[51] Int. Cl.³ ............................................. G01N 21/47
[52] U.S. Cl. .................................. 356/445; 250/571; 356/243; 356/429
[58] Field of Search ................. 356/51, 243, 429, 430, 356/431, 445, 448; 250/339, 571, 572

[56] References Cited

U.S. PATENT DOCUMENTS

| | | | |
|---|---|---|---|
| 3,840,303 | 10/1974 | Clarke | 356/431 |
| 4,160,913 | 7/1979 | Brenholdt | 356/431 |
| 4,277,177 | 7/1981 | Larsen et al. | 356/243 |
| 4,319,847 | 3/1982 | Howarth | 356/243 |

*Primary Examiner*—R. A. Rosenberger
*Attorney, Agent, or Firm*—Donald Carl Lepiane

[57] ABSTRACT

A moisture analyzer sequentially directs a transmitted reference energy beam and a transmitted measurement energy beam toward a mirrored surface background plate as spaced plastic sheets advance along a path through the beams. During the testing period, beams are reflected from the sheets and plate as sheet and plate reflected measured beams and during the non-testing period only from the plate as plate reflected reference and measured beams. The reflected beams generated during the testing period are measured using a detector circuit to determine moisture content of the sheets. The background plate is selected to provide during the non-testing period a value as indicated by the detector circuit that is within the acceptable range for sheets as indicated by the detector circuit operating on the reflected beams generated during the testing period to reduce response time of the detector circuit changing from the non-testing period to the testing period.

12 Claims, 3 Drawing Figures

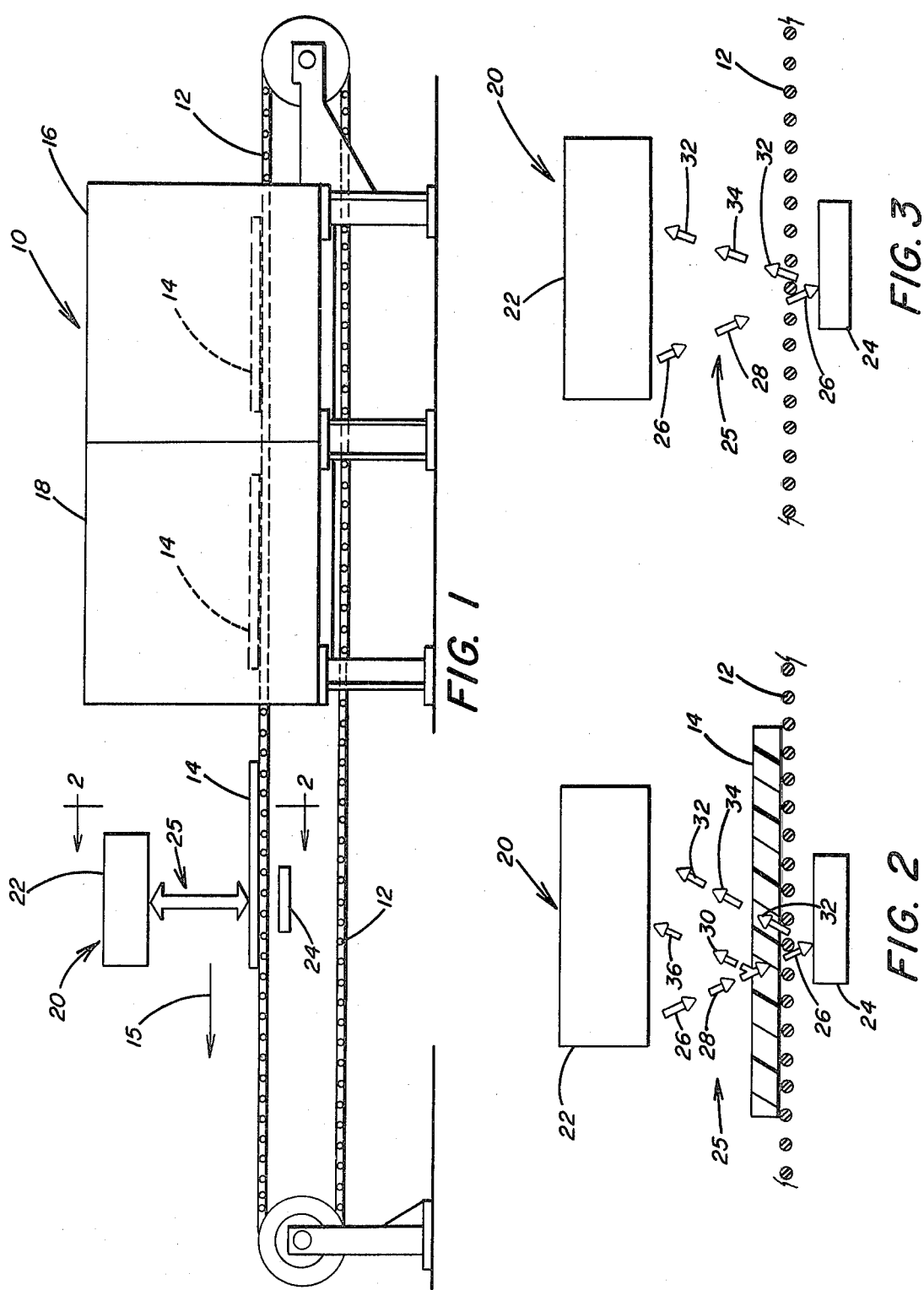

METHOD OF AND DEVICE FOR REDUCING APPARATUS RESPONSE TIME DURING THE TESTING FOR MOISTURE CONTENT IN MOVING SPACED PLASTIC SHEETS

BACKGROUND OF THE INVENTION

1. Field of the Invention

This invention relates to measuring moisture content of a sheet, e.g., a plastic interlayer, used in the manufacture of laminated windows, e.g., structural windows and aircraft or automotive windshields.

2. Discussion of the Technical Problems

In general, in the manufacture of automotive windshields, plastic sheets, e.g., of the type taught in U.S. Pat. No. 4,101,529, are cut from a continuous web, washed, dried and thereafter positioned between a pair of glass plates. The glass plates having the plastic sheet or interlayer therebetween, are subjected to heat and pressure, e.g., as taught in U.S. Pat. Nos. 3,987,449 and 4,046,951 to form a laminated windshield. The moisture content of the interlayer can effect the quality of the finished product, for example, if the moisture content is above about 0.70%, the adhesion of the sheet to the plates is less than desired and could result in delamination. On the other hand, if the moisture content is below about 0.30% by weight, the adhesion to the plates it too great and could lower impact resistance of the windshield.

The plastic sheets are cleaned, dried and positioned between the glass plates to form a subassembly in a controlled environment and the moisture content of the plastic sheet is checked at selected times, for example, after the washing and drying operations. One moisture monitor technique is to manually check selected sheets, e.g., using a Lockwood McClorie infrared moisture analyzer. Although this technique is acceptable, it does not give moisture content of each plastic sheet and usually requires the manual steps of removing the sheet from a conveyor, measuring the moisture content of the plastic sheet and returning the plastic sheet to the conveyor.

Also available are instruments for measuring moisture content in a continuously moving plastic web. Such an instrument is sold by Moisture System Corporation as a Quadra-Beam TM moisture analyzer. Although this instrument is acceptable for measuring moisture content in a moving continuous web, additional considerations are required when measuring moisture content in moving spaced plastic sheets. For example, the response time of the instrument circuit when changing from a non-testing period, e.g., between trailing edge of leading plastic sheet and leading edge of trailing plastic sheet to a testing period, e.g., measuring moisture content of a plastic sheet, should be short so as to accurately and completely measure the moisture content of the upstream sheet. This limitation can be overcome by modifying the instrument circuit, by selectively changing the conveyor speed or reducing the spacing between the sheets. Although these modifications can be made, it would be advantageous to provide a system for automatically inspecting moving spaced plastic sheets that does not require modifying the instrument or the conveying equipment.

SUMMARY OF THE INVENTION

This invention relates to a method of reducing response time of test equipment from a non-testing period to a testing period during which plastic sheets are tested for moisture content using at least one transmitted energy beam. During the non-testing period, the transmitted energy beam is reflected from a background plate as a plate reflected energy beam having a predetermined energy level and thereafter monitoring the plate reflected energy beam by facilities that include an electric circuit. During the testing period, the transmitted energy beam directed toward the background plate is intercepted by a plastic sheet to generate a sheet reflected energy beam and thereafter monitoring the energy of the sheet reflected beam to determine moisture content of the sheet using the electric circuit. The plate reflected beam generated during the non-testing period is selected to have a predetermined relationship to the expected moisture content range for the sheets to reduce response time of the testing facilities from the non-testing period to the testing period. The relationship is determined by the practice of the directing step and the monitoring step.

This invention relates to an apparatus for, among other things, carrying out the above-discussed method and includes a background plate, e.g., a mirrored surface substrate for reflecting transmitted energy beams and facilities for directing energy beams toward the plate and facilities including an electrical circuit for sensing the reflected beam to determine moisture content of the sheet.

In an embodiment of the invention, a Quadra-Beam TM moisture analyzer sequentially directs an infrared reference beam and measured beam toward a mirrored surface. The reflected beams generated during the testing period for acceptable sheets have an expected analyzer reading of about 0.38 to 0.55 which generally corresponds to 0.38% to 0.55% by weight moisture in the sheets. The beams reflected from the mirrored surface during the non-testing period have an analyzer reading of about 0.53. In this manner the response time for the detector circuit of the analyzer changing from the non-testing period to the test period is minimized if not eliminated.

BRIEF DESCRIPTION OF THE DRAWING

FIG. 1 is an elevated side view of a cleaning apparatus which includes a washing station for cleaning plastic sheets and a moisture measuring station incorporating features of the invention;

FIG. 2 is a view taken along lines 2—2 of FIG. 1 illustrating a testing period; and FIG. 3 is a view similar to the view of FIG. 2 illustrating a non-testing period.

DESCRIPTION OF THE INVENTION

With reference to FIG. 1, position 10 includes an endless metal chain conveyor 12 for advancing plastic sheets 14 along a movement path 15 through a washer 16 to clean the sheets 14, a dryer 18 to dry the sheets, and inspection station 20 incorporating features of the invention for measuring percent by weight of moisture in the sheets. As will become apparent, the invention is not limited to the conveyor 12, washing technique, the washer 16, drying technique, or the dryer 18 and any convenient technique or apparatus may be used in the practice of the invention. Further in the following discussion the sheet is a plastic sheet; however, as will be appreciated, the invention is not limited thereto.

With reference to FIGS. 1–3, at the inspection station 20 is a moisture analyzer 22 for measuring moisture content of the sheets in a manner to be discussed below mounted above the path 15 and a background plate 24 mounted below the path 15 for reflecting energy beams 25 from the analyzer 22 back to the analyzer 22. In the following discussion of the invention, the sheets 14 are plasticized polyvinyl acetate sheets used in the fabrication of automotive windshields, e.g., as taught in U.S. Pat. No. 3,808,077, which teachings are hereby incorporated by reference and the moisture analyzer 22 is of the type sold by Moisture System Corp. under the trademark Quadra-Beam TM which is a near-infrared photometric analyzer that analyzes with fixed wavelength of near-infrared energy.

In the practice of the invention, the moisture analyzer 22 is mounted about 8 inches (20.32 centimeters) above the conveyor 12 to direct a transmitted reference infrared energy beam or beams 26 and a transmitted measured infrared energy beam or beams 28 toward the background plate 24. The reference beam 26 is not strongly absorbed by the sheets 14 and is not strongly absorbed by water in the sheets 14. The measured beam 28 is not strongly absorbed by the sheets 14, but is strongly absorbed by water in the sheets 14. A complete discussion of the Quadra-Beam TM moisture analyzer may be found in the instruction manual which is incorporated by reference. The background plate 24 used in the practice of the invention is a square mirror having 5 inches (12.7 centimeters) sides and is mounted about 1 inch (2.54 centimeters) from the upper reach of the conveyor 12 in the path of the beams 26 and 28.

The plastic sheets 14 monitored in accordance to the teachings of the invention have a length of about 4.5 feet (1.35 meters) and a spacing of about 2 feet (0.6 meter) between the trailing edge of the downstream sheet, e.g., leading sheet, and leading edge of the upstream sheet, e.g., trailing sheet on conveyor 12 moving at a speed of about 54 feet/minute (16.2 meters/minute). Sheets 14 having moisture in the range of about 0.38% to 0.55% by weight are considered, for purposes of this discussion, acceptable for use in laminated windshields and correspondingly, the analyzer 22 is conveniently set with a low reading of about 0.38 and a high reading of about 0.55.

With reference to FIG. 2, during a testing period the transmitted reference energy beams 26 and transmitted measured energy beams 28 are sequentially directed toward the movement path 15 as a sheet 14 advances through the beams 26 and 28. As shown in FIG. 2 for a given increment of time and for simplicity of discussion, a transmitted reference beam 26 emanates from the analyzer 22: as a portion of the transmitted measured beam 28 is reflected from the sheet 14 as sheet reflected measured beam 30 and a portion of the measured beam 28 passes through the sheet 14 toward the plate 24; as a portion of the previously transmitted reference beam 26 is reflected from the background plate 24 as plate reflected reference beam 32; as plate reflected measured beam 34 passes through the sheet 14; and as the plate reflected reference beam 32 and sheet reflected reference beam 36 move toward detector cell (not shown) in the analyzer 22. The sheet and plate reflected reference beams 32 and 36, respectively, indicate the amount of reflected energy to be expected. The transmitted measured beam 28 is partially absorbed by the moisture of the sheet 14 and the sheet and plate reflected measured beams 30 and 34, respectively, have less energy than the reflected reference beams 32 and 36. The signal of the reflected beams 30, 32, 34 and 36 is analyzed using detector circuit (not shown) of the analyzer 22 to provide a value related to moisture content of the sheet. When the analyzer senses moisture in the sheet above about 0.55 or below about 0.38, an alarm conveniently sounds indicating that moisture content of the plastic sheet tested is unacceptable.

As the trailing edge of the sheet under test, i.e. the leading sheet, moves downstream of the beams 26 and 28, i.e. during the non-testing period, the transmitted beams 26 and 28 are incident on the background plate 24 and are reflected as plate reflected reference beams 32 and plate reflected measured beams 34. During the non-testing period the mirrored surface plate or substrate 24 provide an analyzer reading of about 0.53. When there is no background plate 24 during the non-testing period, the detector circuit of the analyzer 22 has no load and the readings approach or exceed maximum readout. As the leading edge of the following sheet initially intercepts the beams 26 and 28, to begin the testing period, the detector circuit response, e.g., from about 1.00 to the range of 0.38–0.55 results in unacceptable readings of leading edge portions of the sheet or of the complete sheet. The preceding may better be appreciated from the following example conducted on a plastic sheet having a length of about 4.5 feet (1.35 meters) traveling at a speed of about 54 feet/minute (16.2 meters/minute). A piece of cardboard was placed over the mirrored surface of the background plate and the analyzer displayed a non-testing period reading of 1.19. During the testing period the analyzer displayed a testing period reading which decreased from 1.19 to about 0.80. The previous sheets tested in accordance with the teachings of the invention had analyzer readings in the range of 0.40–0.45. By practicing the instant invention, the load on the detector circuit from the plate reflected beams 32 and 34 during the non-testing period keeps the detector circuit operating in the range of 0.38 to 0.55 and therefore a more accurate moisture content reading of the leading edge portion of the sheet and of the total sheet is obtained.

Background plates 24 having different surfaces reflect beams from the plate having different energy levels and as can be appreciated from the preceding example, a substrate surface having a reading similar to that of the cardboard is not recommended for testing moisture content in moving spaced sheets in the acceptable range of 0.38–0.55, but is recommended if the acceptable range is between about 0.90–1.50 as indicated by the analyzer readings. The use of a cardboard substrate is not recommended as a background plate because it randomly absorbs and releases moisture.

As can now be appreciated, the combination of reflected beams sequentially incident on the detector cell (not shown) of the analyzer 22 need not be as illustrated in FIGS. 2 and 3 and as discussed. For example, a combination of sheet reflected measured beams 30 and plate reflected reference beams 32 and a combination of sheet reflected reference beams 36 and plate reflected measured beams 34 may sequentially impinge on the detector cell (not shown) of the analyzer 22. Further, the transmitted beam and reflected beam in FIGS. 2 and 3 are each shown as single beams but may be a plurality of beams. Still further, the spaced distance between the plate and detector cell of the analyzer can have an effect on the output signal of the detector circuit, e.g., the position of the plate can effect the combination of plate reflected beams and sheet reflected beams and can control the path and path length of the plate reflected beams.

In addition, it can be appreciated that the invention is not limited to a specific background plate, nor to background plates generating reflected beams having energy readings in the expected range of moisture content of sheets to be tested. For example, the background plate used can provide a reading outside the expected range, and if needed, the conveyor speed can be selectively reduced to accommodate the response period of the detector circuit. More particularly, a background plate having a non-testing period readout of about 0.77 or 0.16 can be used if only a reading from the trailing edge of sheets 4.5 feet (1.35 meters) long moving at a speed of 54 feet/minute (16.2 meters/minute) is required. This is because, as shown in the above example, the response time of the circuit, e.g., from 1.19 to about 0.80 is adequate. Although there is contribution from the background plate during testing, it is considered minimum for purposes of the preceding discussion.

What is claimed is:

1. A method of reducing response time from a non-testing period to a testing period of a testing circuit in a device for measuring moisture content in plastic sheets wherein, during the testing period, energy beams are directed toward a sheet, reflected from the sheet in response to the directed energy beams, and the reflected energy beams are detected to provide a reading corresponding to the moisture content of the sheet, comprising the step of:

reflecting the directed energy beams from a specular surface during the non-testing period to provide the testing circuit with energy for producing a reading substantially within the range of anticipated moisture content readings of the sheet.

2. The method as set forth in claim 1 further including the step of:

laminating sheets having a predetermined moisture content to at least one glass panel.

3. The method as set forth in claim 2 wherein said laminating step includes laminating the sheet between two glass panels to provide an automotive windshield.

4. The method as set forth in claim 1 wherein the device sequentially transmits a first transmitted energy beam that is substantially unabsorbed by the sheet material and moisture in the sheet and a second transmitted energy beam that is substantially unabsorbed by the sheet material and is absorbed by the moisture in the sheet, and wherein said reflecting step is accomplished by sequentially directing the first beam toward the plate to reflect a first plate reflecting energy beam and the second beam toward the plate to reflect a second plate reflected energy beam.

5. The method as set forth in claim 4 wherein said directing step includes the step of:

selectively reflecting the first transmitted beam from the sheet as a first sheet reflected energy beam and from the plate as first plate reflected energy beam and the second transmitted beam from the sheet as second sheet reflecting energy beam and from the plate as second plate reflecting energy beam.

6. The method as set forth in claim 4 wherein the transmitted energy beams are infrared energy beams.

7. The method as set forth in claim 6 wherein the anticipated range is about 0.38–0.55 percent moisture by weight in the sheets and the plate reflected energy beams generated during the non-testing period correspond to a moisture value substantially within the range.

8. An apparatus for reducing response time from a non-testing period to a testing period of a testing circuit used in a device for measuring moisture content in a plastic sheet including means for directing energy beams toward the sheet and means for detecting energy beams reflected from the sheet to provide a reading corresponding to the moisture content of the sheet, the apparatus comprising:

a background plate having a specular surface and positioned in the path of the directed beams such that the beams are reflected from the specular surface in the absence of a plastic sheet in the path of the directed beam to produce a reading substantially within the range of anticipated moisture content readings of the sheet.

9. The apparatus as set forth in claim 8 wherein the device sequentially directs the first energy beam that is not absorbed by the sheet or moisture in the sheet and a second energy beam that is not absorbed by the sheet and is absorbed by moisture in the sheet toward said background plate.

10. The apparatus as set forth in claim 9 further including a washer for cleaning the sheets and a dryer for drying the sheets.

11. The apparatus as set forth in claim 10 further including means for conveying a sheet along a path which intercepts the transmitted energy beams.

12. The apparatus as set forth in claim 11 used in combination with means for laminating the plastic sheet to a glass panel.

* * * * *